United States Patent [19]
Saul et al.

[11] Patent Number: 5,783,446
[45] Date of Patent: Jul. 21, 1998

US005783446A

[54] PARTICLE ASSAY USING FLUID VELOCITY GRADIENTS

[75] Inventors: Tom Saul, El Granada; Hans O. Ribi, Hillsborough, both of Calif.

[73] Assignee: Biocircuits Corporation, Sunnyvale, Calif.

[21] Appl. No.: 613,983

[22] Filed: Mar. 4, 1996

[51] Int. Cl.$^6$ .................................................. G01N 21/07
[52] U.S. Cl. .......................... 436/45; 436/165; 436/177; 436/180; 435/7.1; 422/72; 422/73; 422/100; 422/101; 210/789
[58] Field of Search ........................ 436/43, 45, 69, 436/164, 165, 180, 808, 166, 177; 422/61, 64, 73, 81, 100, 101, 104, 72; 210/94, 787, 789, 360.1; 494/10, 37; 435/7.1

[56] References Cited

U.S. PATENT DOCUMENTS

| | | |
|---|---|---|
| 4,135,819 | 1/1979 | Schmid-Schönbein . |
| 4,352,557 | 10/1982 | Schmid-Schönbein . |
| 4,814,282 | 3/1989 | Holen et al. .................. 436/165 |
| 4,865,810 | 9/1989 | Simon ............................. 422/72 |
| 4,916,078 | 4/1990 | Klose et al. ................... 436/165 |
| 5,086,002 | 2/1992 | Hillyard et al. ............... 436/540 |
| 5,173,262 | 12/1992 | Burtis et al. . |
| 5,242,803 | 9/1993 | Burtis et al. ................. 435/7.92 |
| 5,310,523 | 5/1994 | Smethers et al. .............. 422/57 |
| 5,523,238 | 6/1996 | Varon et al. .................. 436/69 |

OTHER PUBLICATIONS

Brown, "The Physics of Continuous Flow Centrifugal Cell Separation," Artificial Organs (1989), 13:4–20.

Link and Springer, "Light Scattering From Dilute Polymer Solutions in Shear Flow," Macromolecules (1993), 26:464–471.

Kume et al., "A new Apparatus for Simultaneous Observation of Optical Microscopy and Small–Angle Light Scattering Measurements of Polymers Under Shear Flow," Acta Polymer (1995), 46:79–85.

*Primary Examiner*—Long V. Le
*Attorney, Agent, or Firm*—Cooley Godward LLP

[57] ABSTRACT

Methods and cartridges are provided for the detection of analytes in a sample by using fluid velocity gradients. In the subject methods, the assay medium is prepared by combining sample suspected of containing analyte with a reagent composition which includes at least one of particles and specific binding pair members ("sbpm's"). A circumferential fluid velocity gradient and vertical fluid velocity gradient are applied to the assay medium to affect the formation of agglutinates. The sizes of the resulting agglutinates are related to the velocity gradients. The level of agglutination is detected to determine analyte presence in the sample. In general, a cartridge for employing the assay comprises two spaced apart parallel plates defining an assay area and trough area there between. A sample port and optically clear window are provided. At least one of the plates is connected to a rotational driver to rotate the plate in a direction counter to the position of the other plate.

10 Claims, 6 Drawing Sheets

NEGATIVE 1/1
10μl

*FIG._8A*

POSITIVE 1/1
10μl

*FIG._8B*

NEGATIVE 1/1
6µl

FIG._8C

POSITIVE 1/1
6µl

FIG._8D

PARTICLE ASSAY USING FLUID VELOCITY GRADIENTS

TECHNICAL FIELD

The technical field of this invention is the detection of analytes by particle agglutination assays.

BACKGROUND

In the field of immunodiagnostics, there is a great need for methods of assaying a wide range of large and small molecules in a simple and accurate manner and which can be incorporated into inexpensive, disposable, semi-quantitative devices. Particle assays are one type of assay which can be used to detect a wide range of molecules. In particle assays, a liquid assay medium may comprise assay elements including analyte and a reagent composition comprising at least one of particles and specific binding pair members (sbpm's). The mixing of the assay medium increases interactions of the assay elements resulting in binding analyte and assay elements in the reagent composition together to form agglutinates in relation to the amount of analyte present. The separation of these agglutinates from non-agglutinated elements greatly facilitates detection of agglutination levels.

In the health care field, a wide variety of particles are detected in particle assays, including red blood cells in agglutination assays for determination of cell type and compatibility between a patient and organ donor; latex, charcoal and gold particles coated with antibodies for various antigens causing infectious diseases such as hepatitis, cytomegalovirus, mononucleosis, syphilis, staphylococcus and to diagnose various disfunctions, cell types and protein levels including D-dimer, rheumatoid factor, or the like.

With the increasing cost of healthcare, it is desirable to provide assay procedures which limit the cost of labor and materials necessary to run the assays. Savings can be realized with assay protocols which are easy to perform yet relatively ensure accurate determination of analyte. Therefore, assays which employ a single simple mechanism to facilitate mixing and binding of elements in a liquid assay medium would be a great advantage by reducing labor and materials costs. The reactions should involve minimum interaction by the user to perform the steps of the assay.

Furthermore, assay methods which include a mechanism to control the relative distribution of agglutinates and non-agglutinates would allow for easy readouts, avoid subjective determinations of results and provide for semi-quantitative results. In many visual assays, agglutinates are viewed by the naked eye of a user. The visual assays often require the skill of costly and highly trained individuals and the results are subjective and often difficult to interpret. Assays which employ a means to separate agglutinates, on the other hand, allow for objective and sensitive determination of results by individuals with low technical expertise.

The devices which incorporate such assays should also be simple to use, requiring only a single step addition of sample by the user and minimal attendance. The devices should facilitate the mixing and binding of elements into agglutinates, separation of agglutinates and provide for optical readings. Such systems may have reagents pre-dried into specific areas and allow for rehydration upon sample addition. The devices further include an automated mixing means therewithin for promoting the rehydration of reagents. In order to maintain accuracy, the devices may provide a means of self-metering the amount of sample which participates in the reaction. In this manner, there is less need for precise pipetting of sample by the user. Furthermore, the devices herein are configured to fit into automated instruments which can read various optical assay results, including scattering, diffraction patterns, optical density, and the like.

There is growing interest in assay procedures which can be performed either at the point-of-care or near to the patient, thus avoiding the need to send samples to large clinical laboratories. To meet this demand, the methods should be able to be run in small, portable disposable devices. The devices which run such assays should be adapted for use in diverse settings, for example doctor's offices, hospital and microbiology laboratories, veterinarian laboratories, clinics, rest homes, individuals' homes, industrial quality control sites and facilities in developing countries.

In response to the need for efficient and versatile assays and their disposable devices, several assays and devices have been constructed. Some of these assays use mechanisms such as force fields to control the flow of a liquid assay medium and to facilitate the steps of the assay.

Uses of centrifugal force to promote fluid flow are known. Burtis, U.S. Pat. No. 5,173,262 discloses such a use of centrifugal force in a rotor. The rotor includes a loading chamber located in the center of the rotor. Measuring and overflow chambers are located at radial distances from the center. During the assay, centrifugation of the entire rotor urges the liquid in the rotor through the various chambers. Furthermore, centrifugation has been used in assays to separate sample components such as cells from plasma in blood samples. Centrifugation in assays is generally described in The Physics of Continuous Flow Centrifugal Cell Separation, R. I. Brown, *Artificial Organs*, 13(1):4–20, 1989.

However, movement of the liquid by centrifugation alone does not promote the steps of the assay including mixing of particles. Centrifugation also fails to separate bound and unbound particles. In centrifugation, assay elements flow at a rate dependent on their density. Agglutinated particles, however, have the same density as their non-agglutinated counterparts and therefore do not separate by centrifugation. Thus, it would be advantageous, to use a force field in the assay medium which would affect rate of flow based on the size of the assay element, instead of density.

The field of polymer physics uses shear forces to create velocity gradients in liquids and study various polymers. In general, shear forces are created by movement of a surface relative to an opposing surface with liquid disposed therebetween. This movement results in velocity gradients in the liquid. Some of the art describes double cylinder shear cells to create fluid movement and shear flow.

The article, Light Scattering from Dilute Polymer Solutions In Shear Flow, by A. Link and J. Springer, *Macromolecules*, 26, 464–471, 1993 describes shear flow in a double cylinder cell to cause molecular deformation of viscous solutions of polystyrene. In addition, a set of rotating parallel plates is used to create fluid flow and shear force in polymer mixtures, as described in the article, A New Apparatus For Simultaneous observation of Optical Microscopy And Small-Angle Light Scattering Measurements of Polymers Under Shear Flow, by T. Kume, et al. *Acta Polymer*, 46, 79–85, 1995. The prior art describing shear force in polymer mixtures do not indicate that shear force can be applied to facilitate the steps in particles assays.

It would be advantageous to use shear force to create velocity gradients in assay mediums, if the gradients were to facilitate mixing of assay elements and thus rehydration of dried elements. Such velocity gradients would further be useful if they would increase particle interactions and facilitate particle binding. Finally, if differently sized particles were to separate along the velocity gradients, then agglutinates may be separated from non-agglutinates through the use of these gradients. Until the present invention, no such assays and their devices have been suggested or developed.

On the contrary, in Schmid-Schonbein, U.S. Pat. Nos. 4,135,819 and 4,352,559, a shear force is applied to blood samples in a manner which inhibits the formation of aggregates. The device is used for analysis of blood subsidence and not for particle assays. A tub and cone shearing device as described in this invention, discourages the binding of particles and destroys existing aggregates during the shearing stage. In Schmid-Schonbein aggregation of particles occurs only after the shear force is turned off or reduced to a residual amount.

It would be advantageous for assay procedures to incorporate shearing force to create velocity gradients and have these gradients influence fluid flow to induce the mixing of assay elements and thus rehydrating dried elements, promote the binding of particles and separate differently sized agglutinates and non-agglutinates. It would further be desirable to provide a convenient device in which to perform the assay in a rapid, single-step manner which may be at the point-of-care of the patient.

RELEVANT LITERATURE

Patents involving the use of microbeads and various optical or other methods for measurement include U.S. Pat. Nos: 4,080,264; 4,115,535, 4,164,558; 4,174,952; 4,340, 564; 4,351,824; 4,521,521; 4,568,644; 4,582,810; 4,690, 906; 4,695,537; 4,711,841; 4,716,123; 4,738,534.

U.S. Pat. Nos 4,181,636 and 4,362,531 discuss various agglutination assays.

U.S. Pat. No. 5,086,002 and International Publication No. WO 91/04492 describe agglutination assays with cross-linking reagents for erythrocytes.

Immunoassays are generally described in: Collins, Alternative Immunoassays (John Wiley 1985); Freytag, "The Future of Immunodiagnostics," J. Clin. Immunoassay (1991) 14:239–244 and Gosling, "A Decade of Development in Immunoassay Methodology," Clin. Chem. (1990) 36: 1408–1427.

SUMMARY OF THE INVENTION

Methods and cartridges are provided for the detection of analytes in a sample by using fluid velocity gradients. In the subject methods, the assay medium is prepared by combining sample suspected of containing analyte with a reagent composition which includes at least one of particles and specific binding pair members ("sbpm's"). A circumferential fluid velocity gradient and vertical fluid velocity gradient are applied to the assay medium to affect the movement and binding of the analyte, any particles present and any sbpm's present. Analyte and assay elements in the reagent composition are allowed to specifically bind together to form agglutinates. The sizes of the resulting agglutinates are related to the movement of the elements under the velocity gradients. The application of velocity gradients may allow for separation of agglutinates and non-agglutinates. The agglutination is detected to determine analyte presence in the sample.

Furthermore a cartridge is provided for employing these particle assay methods comprising two spaced apart parallel plates defining an assay area and trough area therebetween. A sample port on one of the plates feeds liquid sample into the assay area. On at least one of the plates there is a driver connection means which connects the plate to a rotational driver to rotate the plate in a direction counter to the position of the other plate, thus creating at least two fluid velocity gradient in the liquid between the plates, one circumferential and the other vertical velocity gradients. To provide for viewing the presence of agglutinates as indicative of the presence of analyte, an optically clear window is provided on one of the plates

BRIEF DESCRIPTION OF THE DRAWINGS

FIG. 8 (a), (b), (c) and (d) are photomicrograph of agglutinates in assay for E. Coli 0157:H7 with latex particles coated with antibodies for E. Coli 0157 and latex particles coated with antibodies for E. Coli H7. Separation of agglutinates from non-agglutinates are shown in FIG. 8(d).

DESCRIPTION OF THE SPECIFIC EMBODIMENTS

Particle assay methods and a disposable assay cartridge for their use are provided for determining the presence of an analyte in an assay medium which is subjected to fluid velocity gradients. In the subject methods, the assay medium is prepared by combining assay elements including analyte and a reagent composition including at least one of particles and specific binding pair members ("sbpm's"). In some assays, the analyte is the particle and the particles are not included as separate components to the reagent composition and sbpm's are included. A circumferential fluid velocity gradient and vertical fluid velocity gradient are applied to the assay medium to affect the movement and binding of the analyte, any particles present and any sbpm's present. Analyte and assay elements in the reagent composition are allowed to specifically bind together to form agglutinates. The sizes of the resulting agglutinates are related to the movement of the elements under the velocity gradients. The application of velocity gradients may allow for separation of agglutinates and non-agglutinates. The presence of agglutination is detected to determine analyte presence in the sample.

Furthermore a cartridge is provided for employing these particle assay methods. In general, the cartridge comprises two parallel plates which are spaced apart from each other. A sample to port on one of the plates feeds liquid sample an assay area which is intermediate between the plates. On at least one of the plates there is a driver connection means which connects the plate to a rotational driver to rotate the plate in a direction counter to the position of the other plate, thus creating at least two fluid velocity gradients in the liquid between the plates, one circumferential and the other vertical. To provide for viewing the amount of agglutination as indicative of the presence of analyte in the sample, an optically clear window is provided on at least of the plates. Surrounding the assay area is a trough for collecting excess liquid.

In the assay methods of the present invention, sample which is suspected of containing analyte is combined with a reagent composition in an assay medium. The assay medium thus will include liquid sample, and optionally buffer and other solvents.

One may use any type of sample in any kind of liquid in carrying out an agglutination assay in the device. For the purposes of the subject invention, the liquid and sample are referred to as "liquid sample". Physiological samples include blood, serum, plasma, urine, saliva, spinal fluid, lysate, nasal pharyngeal aspirates, etc. Ecological samples include water, soil, waste streams, organisms, etc. Food samples include meat, dairy products, plant products, other organic matter, etc. In addition, samples may include drugs or drug contaminants or cell culture extracts.

The analyte may be any compound which can be detected and is an entity of a specific binding pair, either ligand or receptor. The term "receptor" has traditionally been arbitrarily used. The origin of the term "receptor" referred to surface membrane proteins, where the compound which bound to the surface membrane protein was referred to as a ligand. For the purposes of the subject invention, one may refer to any one of two molecules which have a significant affinity for each other as the receptor, where the binding constant will usually be at least about $10^5$ mol$^{-1}$. Receptors may be naturally occurring, such as enzymes, lectines, surface membrane proteins, antibodies, recombinant proteins, and the like. Receptors may also be synthetic, such as nucleic acids, c-glycosides, carbohydrates, gangliosides, chelating compounds, and the like.

The analyte may be any type of compound so long as there is a complementary binding member, for example small organic molecules, peptides, proteins, sugars, nucleic acids, complex carbohydrates, viruses, bacteria particles, lipids and combinations thereof. The analytes will frequently include both naturally-occurring and synthetic drugs, various components of animals, including humans, such as blood components, tissue components, and the like; microorganisms, such as bacteria, fungi, protista, viruses, and the like; components of waste streams or products or contaminants of such products in commercial processing; components in the environment, particularly contaminants, such as pesticides, microorganisms, and the like.

Prior to introduction into the assay medium, the sample may be subjected to pre-treatment. Choice of pretreatment, if any is required, depends upon the nature of the sample. Types of pretreatments include extraction, distillation, chromatography, gel electrophoresis, dialysis, dissolution, centrifugation, filtration, cell separation, and the like. When using blood samples, one may desire to remove red blood cells to provide plasma or serum by adding a cell lysing reagent to the blood, but their removal is not always necessary.

The analyte is combined with a reagent composition which may include particles. However if the analyte is the particles, then the reagent composition does not include particles. The particles may be synthetic or naturally occurring in nature and may be in a liquid or dried form in an assay area. Synthetic particles may be made of a variety of materials which are then functionalized for linking one entity of a specific binding pair to the particle surface. Materials of interest include various plastics, such as acrylics and polystyrene, liposomes, polymerized liposomes, polymerized liposomes, or other polymerized particles, e.g. polydiacetylenic materials, paramagnetic or magnetic materials such as iron oxide particles, glass such as controlled pore glass, silica, inert particles, latex, starburst dendrimers, long chain polymers such as sugars which are water soluble, colloidal metals, e.g. colloidal gold, zeolites, carbon and graphite. Naturally occurring particles include blood cells, immune cells, tissue cells, bacteria, eukaryotic cells, and the like, particularly red blood cells, i.e. erythrocytes. In assays including these naturally occurring particles, typically the analyte will be the particles.

The number of particles used in an assay will depend on the binding capacity of the particle, i.e. the specific binding pair entity on the binding surface. The number of particles will typically be the number of particles required for binding and for a detection level above background. Normally, between about 1000 and $10^6$ particles will be sufficient for a particular assay. However, where specific binding occurs, fewer than 100 particles may be used. In principle, a single particle could be detected where a detector was sufficiently sensitive to distinguish the resultant agglutination from the background noise. The particles will range in size from about 0.001 to 1000 μm, typically from about 0.01 to 100 μm, more usually from about 0.1 to 10 μm.

The individual particles may have particular characteristics including optical densities, sizes, shapes, refractive indexes, or colors which differ from that of various other assay components. The particles may also be fluorescent whereby the fluorescence can be detected. These unique characteristics allow the assay to be performed directly on the sample and various sample components need not be separated from the sample. For example, where the sample is whole blood, particles may be added directly to blood.

Alternatively, more than one type of particle can be used in an assay to detect more than one type of analyte. For example, a first particle, such as a latex particle, can be added to an assay and red blood cells can be used as a second particle.

Prior to use in the assay, it may be useful to stabilize the particles with reagents, e.g. aldehydes to fix red blood cells. Stabilization of particles may assist in preserving the particles, especially during mixing and separation steps.

It may be further necessary to functionalize the particles in order to provide for a member of a specific binding pair on the particle surface. Conventional functionalization techniques are adequately known in the literature and need not be exemplified here. The number of functional groups on each particle to bind the binding pair member will be at least one and may be as many as ten or more functional groups per particle. Various techniques may be used to provide for a predetermined average number of functional groups capable of binding to the binding pair member and controlling the average number of members bound to the particles. Techniques, such as site-specific illumination for photoactivation, controlled kinetics and chemical blocking can be used for providing a relatively sharp distribution of the ratio of binding entities to particle.

In some embodiments of the present assay procedure, specific binding pair members ("sbpm's") are included in the reagent composition in a liquid or dried form in an assay area and combined in the assay medium. These sbpm's provide for specific binding of the particles and/ or analyte.

In one embodiment of in the subject invention, the sbpm's is a cross-linking agent. As a cross-linking agent, the sbpm's provide for cross-linking of the particles in an amount proportional to the amount of analyte in the sample. In another embodiment, the sbpm's compete with analyte for binding to the particles, wherein binding of sbpm's to analyte is inversely related to the amount of analyte present. Sbpm's in competition assays are especially useful where the analyte is monovalent. The particular sbpm's included in the assay medium will depend on the type of particles used and the analyte to be detected, as well as the particular binding format desired. The amount of sbpm's included in the assay medium will not be critical, so long as the amount included is not a limiting amount with respect to the binding interactions which may occur in the assay medium.

The sbpm will comprise at least one binding moiety for at least one type of particle. Through the binding moieties, the sbpm's will bind to particles. In particular, the cross-linking sbpm's may include several binding moieties for one type of particle to bind several of the same type of particles together, e.g. several red blood cells bound together. The cross-linking sbpm's may also include binding moieties for several types of particles and thus can also bind a plurality of types of particles together, for example one type of particles is bound to a singular particle of another type, e.g. several red blood cells bound to a single latex particle or several colloidal gold particles bound to a single red blood cell. The particle binding moiety employed on the competitive and cross-linking sbpm's may be an antibody or binding fragment thereof, e.g. Fab or F(ab)$_2$, lectins, peptides with specific affinity for the particle surface, and the like.

The sbpm's may also have analyte binding moieties attached thereto for binding of particles to analytes. The particular analyte binding moieties of the sbpm's will depend on the analyte of interest. The moiety may be an antibody or a specific binding fragment thereof.

The assay medium may also be combined with dried reagents, especially where the sbpm's or particles are dried. These dried components may affect the viscosity of the assay medium. For example dried sugars may be included to regulate the viscosity of the assay medium.

After the assay elements are combined the assay medium is exposed to fluid velocity gradients. Typically, the fluid velocity gradients include at least one circumferential and one vertical velocity gradients produced by a shearing force applied to the assay medium. The shearing force is created by a source at the opposing boundaries of the liquid medium.

The shearing may be from any convenient source which produces velocity gradients as long as the resulting velocity gradients allow for mixing, binding and separation of assay elements. One such source comprises a cone rotating inside of another cone, with the assay medium located between the cones. Preferably, the shear is created by two opposing plates at the liquid assay medium's boundaries and at least one of the plates rotate in directions counter to the position of the other plate. In one embodiment, one plate is rotated and the other plate is held motionless. In another embodiment, both plates spin in directions which are counterclockwise to each other.

Where the shearing source is at least one rotating plate, the circumferential fluid velocity gradient occurs from the center of the shearing force, i.e. the axis of rotation, and radially expands outward therefrom. The vertical fluid velocity gradient begins at one boundary of the liquid medium and expands toward the opposite boundary proximal the points of application of the shearing force.

The magnitude of the velocity gradient is controlled by the amount of shear stress applied to the assay medium and depends on the type of liquid assay medium, i.e. viscosity of the medium, and type of assay elements included in the medium. The amount of shear stress applied should create velocity gradients which promote mixing of the analyte, sbpm's and particles. The mixing causes rehydration of any dried particle and sbpm's that are predisposed in the assay system. Movement of the analyte, sbpmn's and particles in the velocity gradients also affects the interactions of these assay elements. Therefore, magnitudes of the gradients are controlled to increase these interactions, and thus facilitate binding of assay elements to form agglutinates.

Furthermore, the amount of shear stress applied may allow for the separation of bound from unbound elements through the velocity gradients. Although Applicants do not want to be held to theory, the separation of agglutinates from non-agglutinates may be based on size, and not density, whereby smaller agglutinates contact the peak of the velocity gradients and larger agglutinates contact the range of velocities of the gradients. Smaller elements appear to travel faster along the peak of the flow path and larger elements travel at a slower rate along the lower gradient of the flow path. Movement of the assay elements is observably from the outer perimeter of the assay medium towards the center of the shearing source. Thus, as the assay progresses, unbound elements, i.e. agglutinates, are detected proximal the center of the shearing source and larger bound elements, i.e. agglutinates are found farther away from the center.

Where the shearing source is at least one rotating plate, the rate of rotation of the plates is generally between about 1000 to 0.1 rpm, typically about 500 to 1 rpm and usually 100 to 10 rpm.

After sufficient time, e.g. 10 sec to 10 hours, for the elements to react to form agglutinates, if any, or during the agglutination of assay elements, the size of the agglutinates is detected. Determination of the amount of agglutination may comprise a single measurement or series of measurements, e.g. to determine rate or end-point, depending on the assay. Further, one may read the agglutination amount and compare it to the agglutination amount from a control, where the control comprises a predetermined amount of analyte, including no analyte. To detect agglutination, the assay area is irradiated so as to obtain a detectable signal.

Any convenient optical detecting means may be employed. Some conventional means includes detecting light scattering of the agglutinates, detection of fluorescence, refraction, optical density, and the like.

Optical diffraction may be used wherein light which is applied to the elements of the assay medium is diffracted to form diffraction patterns. Agglutinated and non-agglutinated elements of varying sizes create distinct diffraction patterns. These patterns are analyzed for determination of agglutination level. Optical diffraction is described in copending application, Ser. No. 08/326,978, filed Oct. 21, 1994, the contents of which is incorporated herein by reference.

Imaging of the agglutinates may also be used to observe the level of agglutination. The imaging system may include microscope optics and a detector, e.g. CCD array detector. The optics usually provide an image magnification of 10× or greater, and preferable 13×. The optics may also include various filters. The image is then analyzed for agglutination level.

Image analysis usually consists of background leveling and calculating the amount of agglutination present. In background leveling, variations in the background illumination are canceled. One such technique is flat-fielding, wherein the original image is divided by an image of the background illumination. This background image may be obtained by several methods, including dilation such that a central pixel is replaced by the brightest close pixel. During dilation, dark pixels are replaced by brighter pixels. Filters may be applied to smooth the image and the degree of agglutination is determined.

One method of calculating agglutination is by area fraction analysis. The steps for analyzing area fraction data for the image consists of distinguishing features, e.g. agglutinated particles from background, counting the features, measuring the area, e.g. size of each feature, calculating the area fraction histogram from the area data, and analyzing the histogram to determine the degree of agglutination.

It is understood that in performing the subject assay method, one may vary the order of the above described steps and obtain the desired results as long as all of the above described steps are included in the method. Thus varying the order of the steps is considered within the scope of the invention. For example, instead of applying the velocity gradients to the assay medium after adding the assay elements, one may add the assay elements while continually applying a velocity gradient to the assay medium. Also, one may wish to add only some of the assay elements to the assay medium, apply the velocity gradients, and then add the remaining elements to the assay medium while applying the velocity gradients.

Several types of devices may be used in carrying out the above described assay methods, as long as the above mentioned velocity gradients and assay conditions are created within the device. Example cartridges for employing the assay are described below.

Specifically, the cartridge comprises two plates which are at least substantially parallel, and preferably parallel to each other. The plates may be any convenient shape including square, rectangular, circular, and preferably circular. The plates may be made of any durable material, including plastic, such as polycarbonate, acrylic, polystyrene; metal; glass; and the like. The plates include inner and outer surfaces. The inner surfaces face each other and may be coplanar, convex, concave or other shapes. The inner surfaces of the plates may be flat or may have surface features which affect the assay condition such as the mixing of analyte, particles, and sbpm's. For example, the surfaces may have troughs, grooves, channels, blades, domes, etc. The plates are rotatably connected to each other at any general location, such as their center or periphery.

The plates may be included in the cartridge through machine molding of the cartridge or by gluing together the parts. In a preferred embodiment, the plates are in rotatable contact with each other proximate their peripheries by a locking mechanism. The locking mechanism comprises a flexible inwardly facing tab including an edge on one of the plates and on the other plate, a rigid outwardly facing tab with an edge. To engage the locking mechanism, the flexible tab bends outward to allow its edge to bias the edge of the rigid tab such the plates are held in close association with each other. The contact between plates is loose enough to allow for one or both plates to rotate in a direction counter the position of the other plate. This non-hermetical seal between the plates may also serve to vent air and gasses from the space between the plates.

The plates are spaced apart from each other to create an assay system therebetween for performing the particle agglutination assays as previously described. The distance between the plates depends on the type of assay and volume of sample required. The distance is also determined by the size of the individual parts located in the assay system, e.g. raised circular platform, overflow trough, etc.

The cartridge includes a means of introducing liquid sample into the assay system between the plates such as an inlet port and a channel. Sample introduction optionally may be by the direct addition to one of the plates by the user prior to engaging the plates together and forming the assay system. Generally, an inlet port is provided on one of said plates and is in fluid communication with the assay system. The inlet port feeds sample and other liquid reagents either directly or indirectly into an assay area.

The inlet port may be any convenient shape for receiving sample into the assay system, such circular, square, rectangular, oval, usually circular. The sides of the sample addition port may be cylindrical or beveled, where the diameter of the top of the port is larger than the diameter of the bottom of the port. The dimensions of the sample addition port will be sufficiently large to receive a volume of sample, where the volume of sample will usually range from 1 to 100 ul. Where the sample addition port is cylindrical, the diameter of the addition port may range from 1 to 5 mm.

In addition to serving as a means to introduce sample to the assay system, the inlet port may serve as a vent to release air and other gasses during the assay. The port may also serve as an interface with an external suction means, e.g. a pump, or a puffer to release air into the assay system.

Beneath the inlet port may be either an assay area so that sample feeds directly from the port into the assay area, or a circumferential trough or sample receiving region so that sample feeds indirectly into the assay area, and preferably a circumferential trough. Where the cartridge has a sample receiving region, the region serves to receive the sample and provide a conduit between the inlet port and the circumferential trough or the inlet port and the circular platform.

The circumferential trough is radially spaced around and in fluid communication with an assay area including a circular raised platform. The trough may serve to receive sample and reagents from the inlet port. The trough may further serve as a convenient location for pre-treatment of sample prior to the sample entering the raised platform, such as dilution of sample, extraction of sample components by precipitation or the like, and modulation of sample temperature, e.g. raising or lowering of sample temperature, as desired for the particular assay being carried out. The trough will collect excess sample that does not enter the raised platform for participation in the reaction. It also collects waste sample, reagent, specific binding pair members and particles.

The depth of the trough will range between about 0.01 to 5 mm, typically about 0.05 to 1.0 mm and more usually about 0.1 to 0.5 mm. The diameter will range from about 0.01 to 5 mm, typically about 0.1 to 1 mm and more usually about 0.5 to 1.0 mm. The volume in the trough may range from 0.1 to 500 µl, more usually 1 to 100 µl and will preferably range from 10 to 50 µl.

The liquid sample will enter an assay area including a raised platform for combination and reaction with other assay elements in an assay medium. The assay area is in fluid communication with the sample introduction means and the trough. The raised platform in the assay area is any convenient shape, and usually circular. The platform is positioned at the axis of rotation of the plates, and typically proximate the center of the two plates. The platform may be formed by a pedestal protruding from the inner surface of one of the plates. In some embodiments, the assay system contains two opposed platforms protruding from each plate and facing each other. The assay area is created in the space between the platform and the opposite plate or, where two platforms exist in the assay system, between the opposing platforms. The height of the platform is sized to create a capillary in the assay area. By capillary is meant that the dimensions of the platform provide for capillary flow of fluid through the assay area, thus allowing sample to be drawn into the assay area by capillary force. The height and diameter of the platform is also sized to permit only a predetermined volume of liquid sample to be drawn into the assay area by capillary forces. Thus the size of the assay area between the platform serves to self-meter the amount of sample and other reagents which participates in the reaction. In this manner, there is less need for exact accuracy in the amount of sample and reagents introduced into the assay system by the user, for example by pipeting through the inlet port. Generally, the distance between the platforms where two platforms are present and between one platform and the inner surface of the plate where one platform is present is between about 0.005 to 0.125 cm usually between about 0.01 to 0.10, and typically about 0.01 to 0.05 inch. The diameter of the circular raised platform is about 0.1 cm to 2.0 cm usually between about 0.1 to 1.5 cm and typically about 0.5 to 1.0 cm. The volume of liquid permitted in the assay area is between about 0.1 to 500 μl, usually between about 1.0 to 100 μl, and typically about 10 to 50 μl.

The assay area may serve multiple functions. First, the assay area contains any of the sbpm's and particles required for the particular assay. The particles and sbpm's may be dried to the surface of the raised platform or in a liquid solvent. Thus, the platform may be a placement site for dry particles, sbpm's, and other reagents during the manufacture of the cartridge. Also optionally contained on the reaction platform may be reagents to modify the sample's pH, redox potential, etc. Second, the platform is the site in which analyte, sbpm's and/or particle bind to their complementary specific binding pair member, thus forming agglutinates. The reaction assay area is additionally the area of separation of agglutinates from non-agglutinates. The presence of agglutination is detected in the assay area to determine the presence of analyte in the sample. Finally, the assay area serves as the location for creation of at least one velocity gradient in the assay medium, e.g. liquid sample or other solvents, by the rotation of at least one of the plates counter to the position of the other plate. In one embodiment, one plate is rotated and the other plate is held motionless. In another embodiment, both plates spin in directions which are counterclockwise to each other.

There may be several velocity gradients in the liquid created by the rotation of the plate(s). Some of the gradients which facilitate mixing, binding and separation of the assay elements include circumferential and vertical velocity gradients. The circumferential velocity gradient occurs from the center and radially expands outward therefrom, preferably across the assay area and across the overflow trough. The vertical velocity gradient begins at the plate which is rotating and expands toward the opposite plate. The gradients are described in the above assay methods section.

The rotation of the plates is by a driver connection means on at least one of the plates. The driver connection means is adapted to connect with a rotational driver including a motor or a planetary gear device. Preferably the driver connection means consists of a plurality of protrusions uniformly spaced around the periphery of the plate. The protrusions are sized to fit into an external planetary gear device.

The planetary gear device consists of a first central rotating portion including a top and bottom. On the central rotating portion's top, usually in the center axis of the rotating portion, there is a drive motor interface which connects with an external motor to rotate the first central rotating portion about its center axis. The central rotating portion additionally includes a plurality of arms extending from the center to engage the cartridges. The bottom of the ends of each arm is adapted to rotatably contact a cartridge on the cartridge's outer surface. The center of the arm ends also have a read hole which corresponds with the optical windows on the cartridges.

Where the cartridge has only one plate which rotates, the planetary gear device further has a stationary platform opposite the central rotating portion which engages the non-rotating plate of the cartridge for holding that plate stationary while the opposite plate rotates. The stationary platform also includes a plurality of read holes which correspond to the optical windows on the cartridges held therewithin. Where the cartridge has a first and second plate that both rotate in directions counterclockwise to each other, the planetary device does not include a stationary platform, but includes a second central rotating portion similar to and positioned opposite of the first central rotating portion. This second central rotating portion is turned in a direction counterclockwise to the spin of the first central rotating portion.

Furthermore, the planetary gear device includes one or two circumferential stationary outer gears to contact each rotating plate of the cartridges. Where the cartridges include two rotating plates, one stationary outer gear contacts one rotating plate, and the other stationary outer gear contacts the other rotating plate. Where the cartridges include only one rotating plate, only one outer gear exists to contact this plate. The outer gear consists of a plurality of protrusions uniformly spaced around the device's periphery and face the central rotating portion of the device. The outer gear protrusions are sized and spaced to engage the protrusions of the drive means on the rotating plates of the cartridges.

When the planetary gear is used, the central rotating portion of the planetary gear with the cartridges therewithin spins from its drive interface. As the central rotating portion and cartridges are turned, the drive mean protrusions on the cartridges' rotating plates engage the outer gear, forcing the rotating plate to rotate. Where the cartridge consists of only one rotating plate, the opposite plate is held stationary on the stationary platform. Where the cartridge includes two rotating plates, the plates spin in the opposite direction.

In this configuration, several cartridges may be engaged on the planetary gear to perform several assays at the same time. Some of the cartridges may be used to perform a control test. Other cartridges in the planetary gear device may be used for the same assay of two samples, or two different assays for the same or different samples. Thus a test panel of assays on related analytes may be conveniently performed to quickly make a diagnosis.

The plate which is not rotated during the assay includes a holding means located on the outer surface of the plate for preventing the plate from moving. Examples of holding means include bearing locks, pins, adhesives, rubber gripping parts, etc. In one embodiment, the holding means is an extension of the plate which connects with an external support. Where the planetary gear device is used, the holding means contacts the stationary platform of the device.

An optically clear window is on one or both of the plates and positioned over or under the raised circular platform. In a preferred embodiment, the plate comprises two opposing raised circular platforms and two opposing clear windows proximal platforms. The optically clear window provides for viewing of the agglutinates and non-agglutinates formed by the particular assay being performed in the assay area.

Optionally, the assay system includes fluid interruption means which are located in various positions in the assay area such as in the circumferential trough to disrupt the flow of fluid into the circular raised platform and around the periphery of the assay system to prevent leakage of fluid from the cartridge. One type of fluid interruption means comprises a hydrophobic area to impede fluid flow over the area. Additional fluid interruption means include removable physical barriers to fluid flow. Some of these barriers can be removed by magnetic forces, and dissolve upon contact with fluid, e.g. soluble plugs of polyethylene glycol, and the like. Preferably the interruption means is a stop junction. As present in the subject cartridge, the stop junction may comprise a capillary intersecting a reservoir at any convenient angle such that the flow of fluid across the stop junction and into the reservoir is impeded. The angle of the floor of the capillary to the reservoir is fairly steep, being at least 60 degrees, and will preferably be about 90 degrees.

A reservoir may be provided proximal the perimeter of the plates adjacent to the stop junction. The is sized to avoid capillary flow therewithin. The reservoir serves to collect liquid which leaves the assay system and prevent liquid from escaping from the interior of the cartridge.

A lubrication area is provided proximal the periphery of the plates adjacent to the stop junction. The lubrication area is a capillary and positioned so that liquid migrates from the tough into the lubrication area. The lubrication area is in fluid communication with the stop junction via a conduit. Therefore as liquid travels from the lubrication area into the stop junction, movement of the liquid is interrupted. The lubrication area serves to make slippery the area between the plates at the lubrication area to facilitate rotation of the plates relative to each other.

The cartridge also optionally includes a detectable code region, such as a barcode, reflective spots, modification of refractive indexes, etc., on the outer surface or inner surface of at least one of the plates, preferably on the holding means. If on the plate's outer surface, the detectable code region may be on the top or bottom of the cartridge. The code serves as a means to identify the cartridge and sample type.

The cartridge optionally has a reference area which serves to provide an indication of the operability of the specific binding pair members and particles being employed. For example, the reference area may comprise dehydrated particles and sbpm's. The reference area may not be in fluid communication with the assay system, so as not to interfere with an assay being conducted with the cartridge.

The cartridge may further include filters located outside of the assay area for separating components of the sample prior to the assay.

Figure 1:
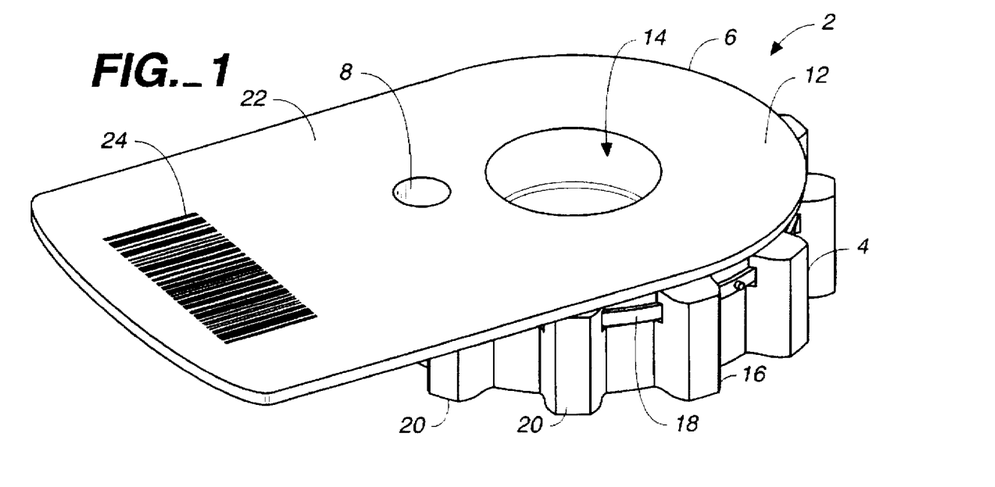
FIG. 1 is a perspective view of a cartridge in accordance with the present invention having a stationary plate and rotating plate rotatably contacting each other.
Figure 2:
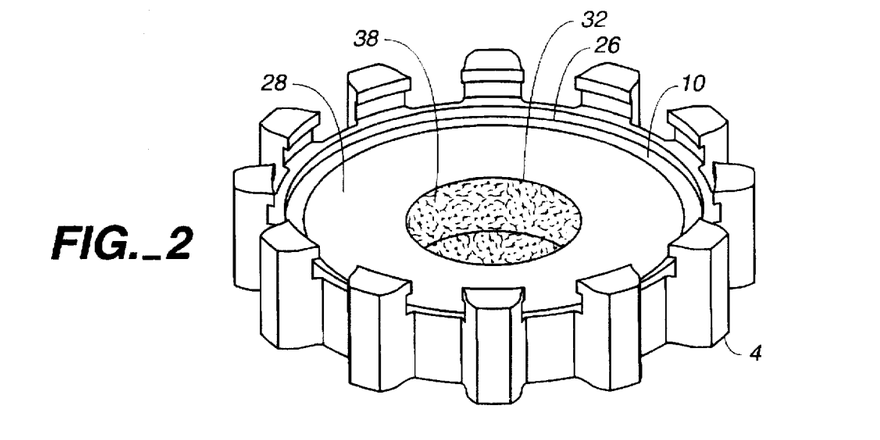
FIG. 2 is a perspective view of a rotating plate of the cartridge.
Figure 3:
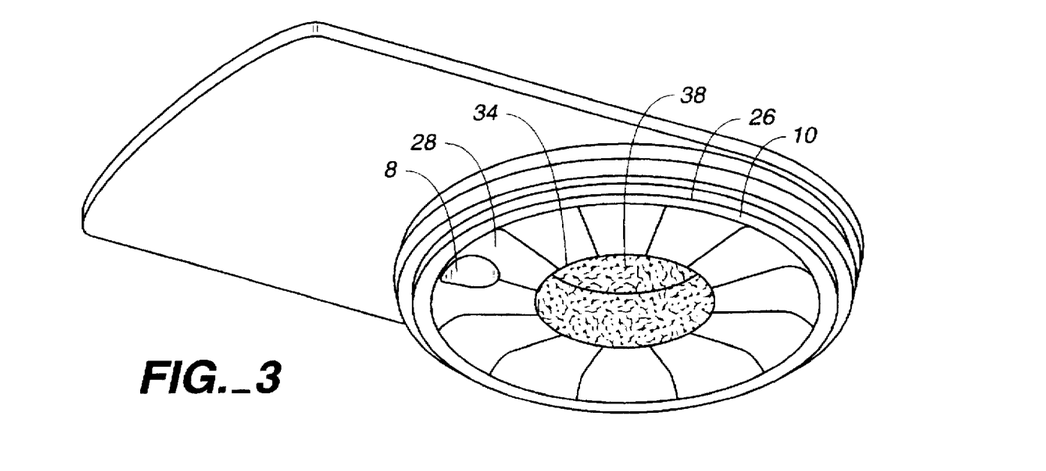
FIG. 3 is a perspective view of a stationary plate of the cartridge.
Figure 4:
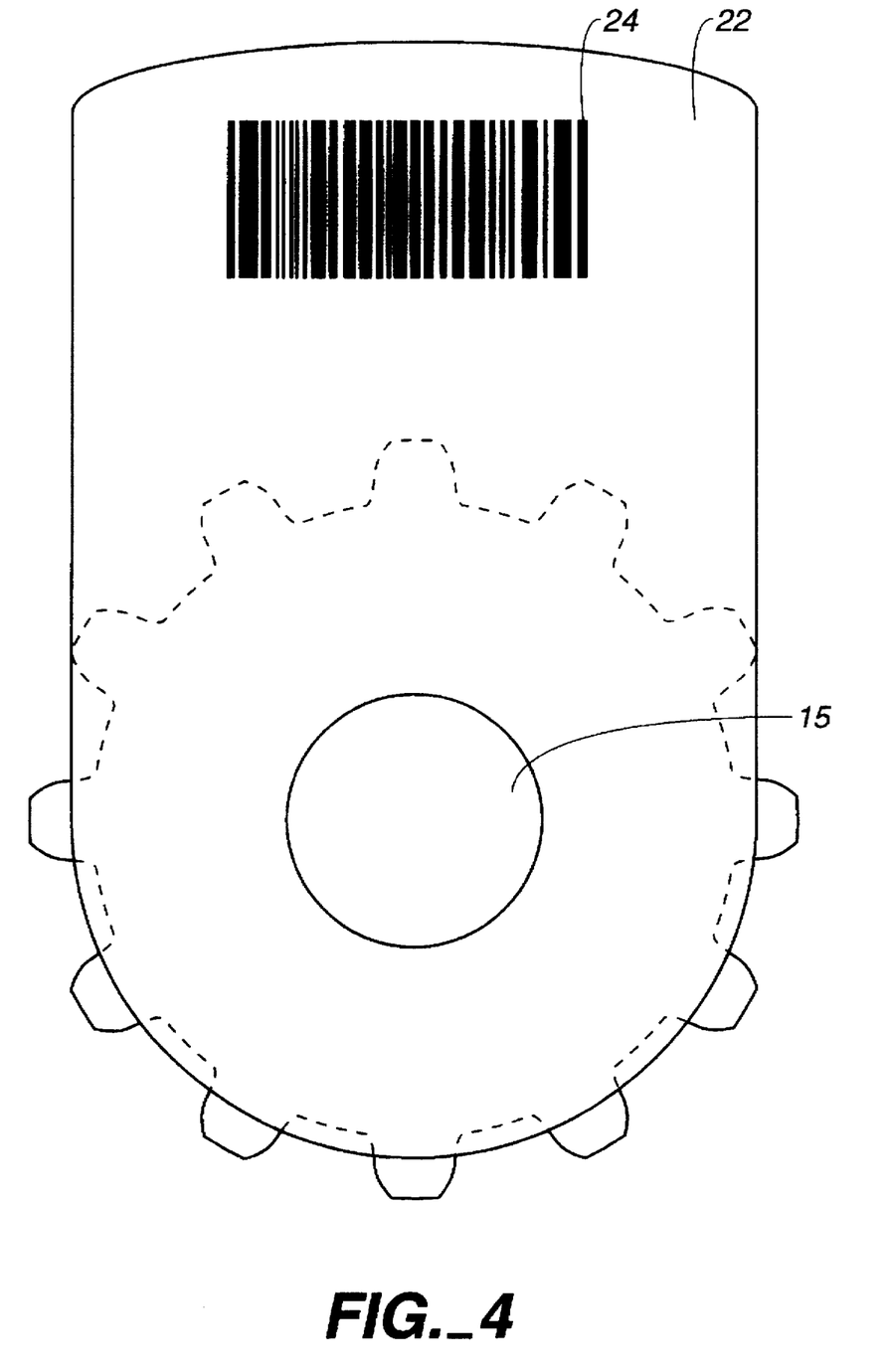
FIG. 4 is an overhead view of the cartidge as in FIG. 1.

The cartridge will now be further described in terms of the figures. In FIG. 1, is depicted a representational view of a disposable assay cartridge 2 with two parallel spaced apart plates, a rotating plate 4 and a stationary plate 6. A port 8 is positioned on one of the plates. In the FIG. 1, the port is on the stationary plate. The port leads to the assay system 10 located between the two plates. The assay system is best shown in FIG. 2 and 3. On the outer surfaces 12 of the stationary 6 and rotating plates 4 are optical windows 14, 15 for viewing the assay system. The optical window of the rotating plate 15 is shown in the bottom plan view of the cartridge in FIG. 4. The periphery 16 of the rotating plate also includes a driving connection means 18 including a plurality of uniformly spaced protrusions 20 around the periphery. The stationary plate includes a holding means 22 extending from the outer surface 12 for preventing the plate from rotating. The holding means 22 in the depicted cartridge includes a bar code 24.

Figure 5:
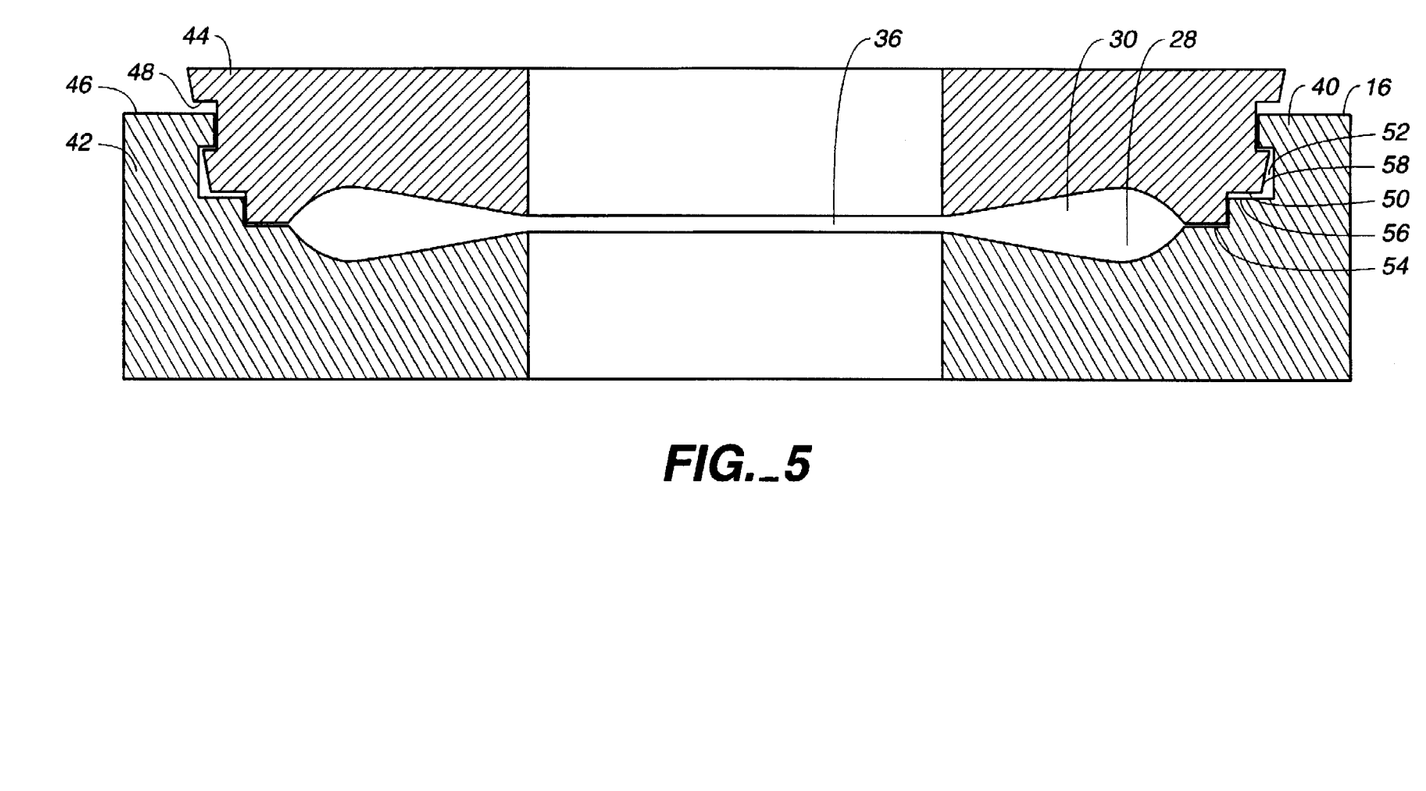
FIG. 5 is a cross-sectional view of the cartridge with a locking mechanism.

The rotating plate is shown in FIG. 2 with an inner surface 26. And the stationary plate is shown FIG. 3 with an inner surface 26. Both plates include a tough 28, 30 located proximal the inlet port 8. The troughs 28, 30 are radially spaced around raised circular platforms 32, 34 on both plates. The platforms 32, 34 define a space therebetween which is an assay area 36, as best shown in FIG. 5. In the assay area, and in particular, on the raised platforms are predisposed assay elements 38 including particles and sbpm's.

The two plates are maintained in rotatable contact with each other by a locking mechanism 40 at the periphery of the plates 16, as shown in the cross sectional view of the cartridge in FIG. 5. The locking mechanism 40 comprises a flexible inwardly facing tab 42 on one of the plates, and a rigid outwardly facing tab 44 on the other plate. Both the inwardly facing tab 42 and the outwardly facing tab 44 have edges 46, 48. In practice, the edge 46 on the inwardly facing tab biases against the edge 48 of the outwardly facing tab to hold the plates in close association with each other.

FIG. 5 also shows a fluid interruption means 50, reservoir 52, and lubrication area 54. The fluid interruption means 50 as shown in FIG. 5 is a stop junction formed by the wall of capillary 56 meeting the wall 58 of reservoir 52 at a sharp angle to resist fluid flow therefrom. Any fluid that may escape is further held in reservoir 52 and prevented from escaping the cartridge. The lubrication area 54 is formed at a contact point between the first and second plates proximal their peripheries. Liquid in the lubrication area serves to make contact slippery and facilitate the rotation of the plates relative to each other.

Figure 6:
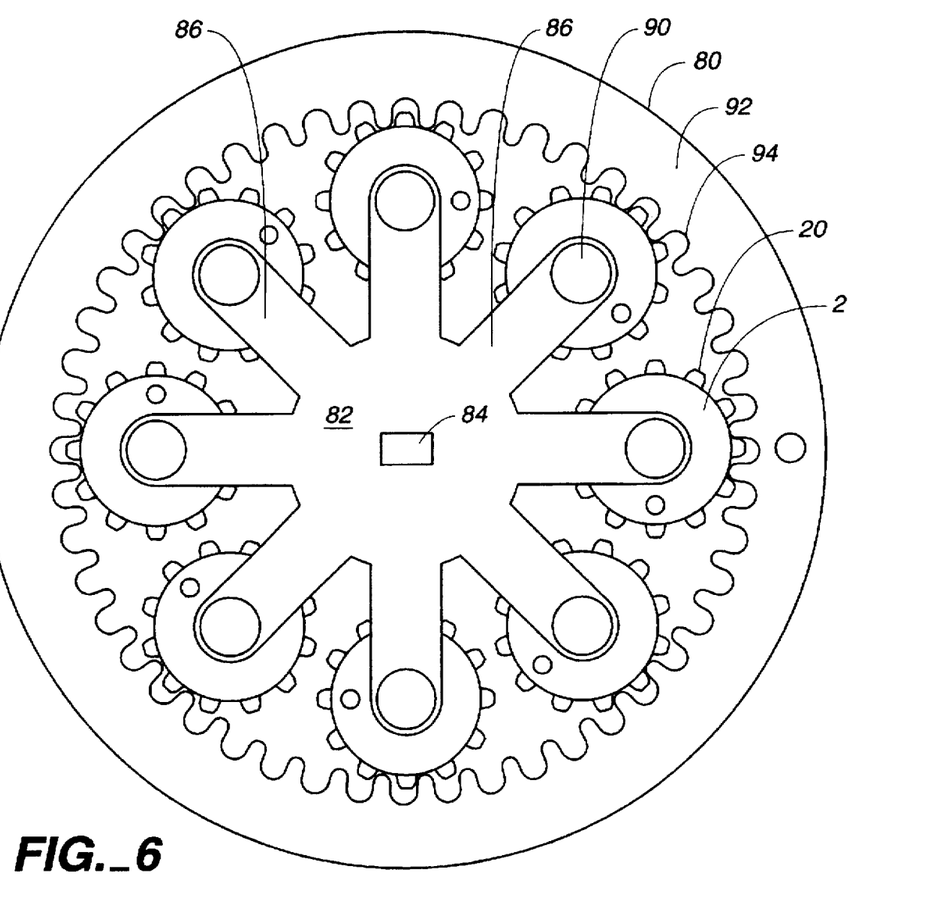
FIG. 6 is an overhead view of the top of a planetary gear device in accordance with the subject invention.

At least one of the plates of the cartridge may be rotated by placing the cartridge in a planetary gear device 80 as shown in FIG. 6. The gear device comprises a central rotating portion 82 which is turned via a drive motor interface 84. A plurality of arms 86 extend from the central rotating portion to contact the cartridges 88 at the end of the arms with a read hole 90 corresponding with the optical windows 14, 15. The gear device also includes a stationary platform 92 contacting the opposite plate as the central rotating portion contacts, and further with read holes corresponding with optical windows on the cartridge (not shown). The stationary platform 92 has a circumferential stationary outer gear 94 which includes a plurality of protrusions to engage the protrusions of the cartridge drive means 20.

Figure 7:
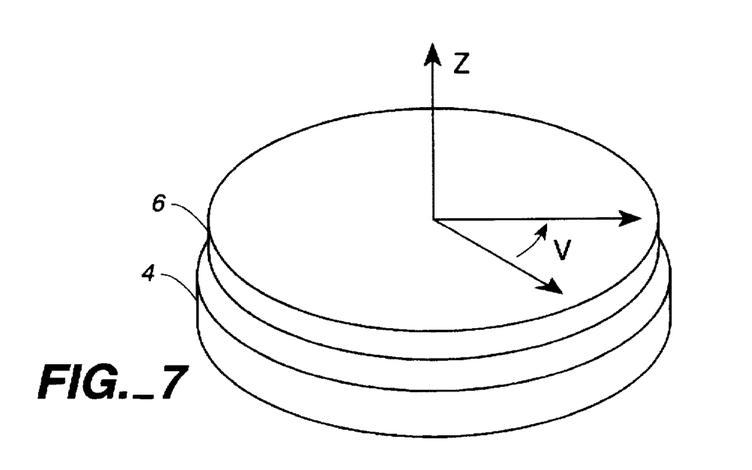
FIG. 7 depicts the direction of flow of a circumferential and vertical fluid velocity gradients created by one rotating plate and one stationary plate.
Figure 8A:
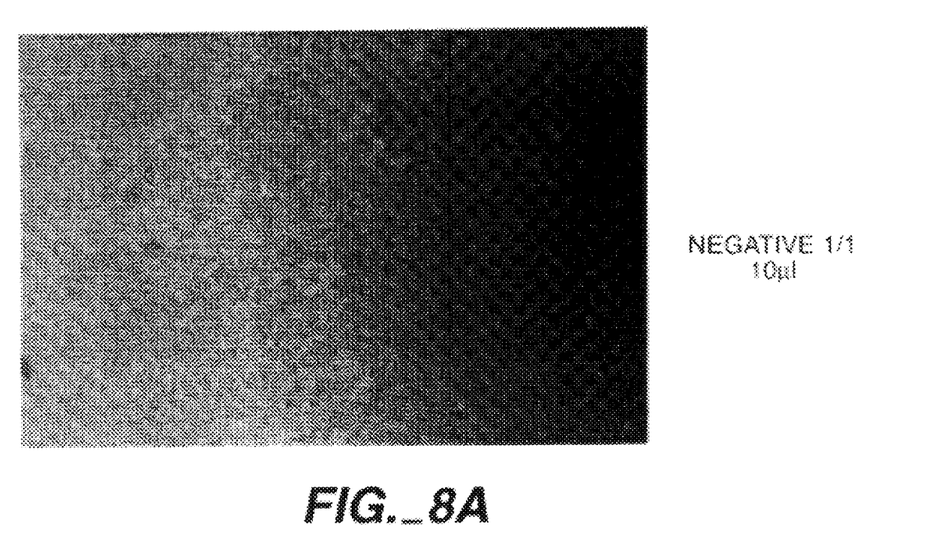
Figure 8B:
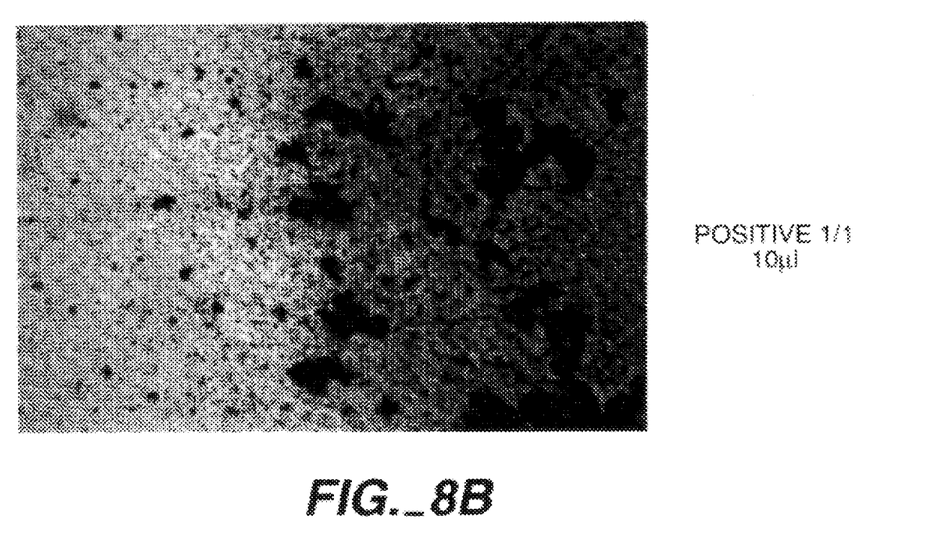
Figure 8C:
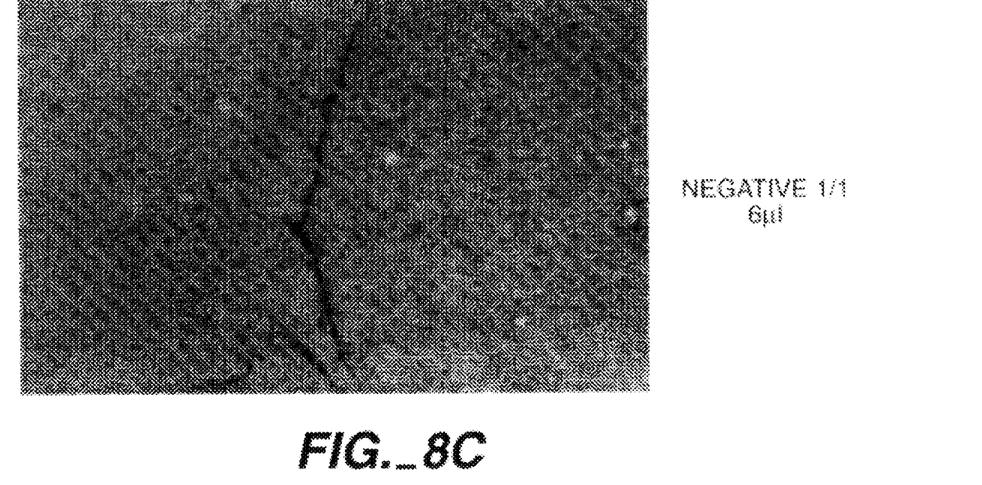
Figure 8D:
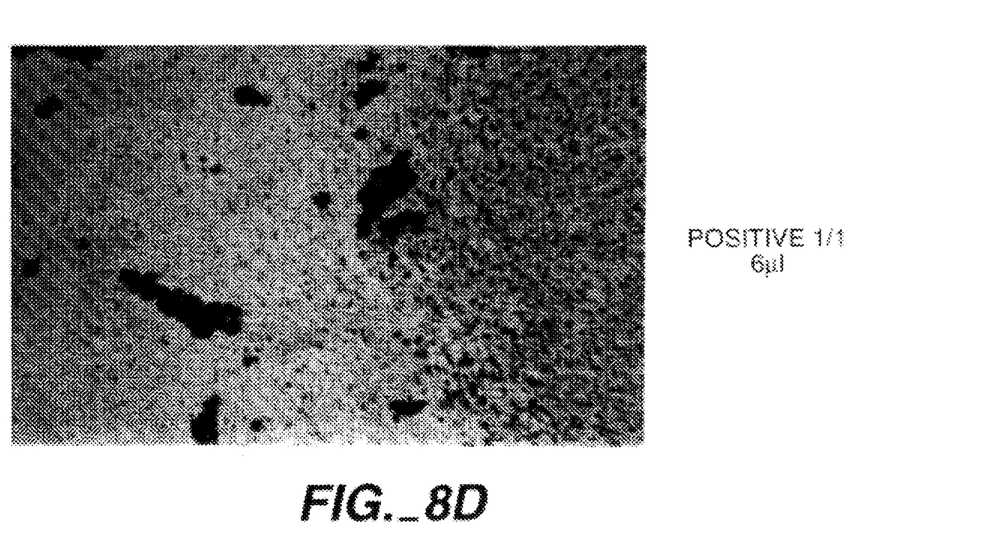

As the cartridge is rotate by the planetary gear device, circumferential and vertical fluid velocity gradients are formed as shown in FIG. 7. Rotating plate 4 and stationary plate 6 creates a vertical velocity gradient in the direction of z and a circumferential velocity gradient in the direction of v.

EXPERIMENTAL

EXAMPLE 1

PARTICLE AGGLUTINATION ASSAY USING FLUID VELOCITY GRADIENTS IN A CARTRIDGE TO TEST FOR *E. COLI* WITH LATEX PARTICLES IN A LIQUID SOLUTION

A particle assay was performed for detection of *Escherichia coli* 0157:H7 on a cartridge consisting of one rotating plate and one stationary plate. Assay elements including sample with analyte and latex particles were provided by Remel Corporation, 12076 Santa Fe Drive, Lenexa, Kans. 66215, in assay kit Catalog No. 24-250.

Sample solution was prepared with a formalin-killed cellI suspension of *E. Coli* 0157:H7 (positive control) derived from ATCC® strains 43889 and 43890 in buffered saline and a formalin-killed cell suspension of non-toxigenic *E. coli* which is not 0157:H7 in buffered solution (negative control). Sample was brought to room temperature and diluted with 0.1M glycine (provided by Sigma Chemicals, St. Louis, Mo. 63178, Catalog No. G-7126) and 0.1M NaCl (provided by Mallinckroft Chemicals, Paris, Ky. 40361) in $dH_2O$.

Two types of particles in a liquid solution were next brought to room temperature for use in the assay. Particles consist of *E. coli* 0157 pooled rabbit antibody coated latex particles suspended in buffered solution with 0.01% thimerosal and *E. coli* H7 pooled rabbit antibody coated latex particles suspended in buffered solution with 0.01% thimerosal.

Prior to contacting the plates of the cartridge to one another via a locking mechanism, 15 ul of liquid sample is pipetted directly onto the raised platform of one of the plates. Particles in the amount of 5 µl of the particle solution where added to the same raised platform.

In order to maintain contact between the two plates, 7 µl of buffer is added to the lubrication area of the plates to create a slight holding force between the plates. The plates are placed into rotatable contact with each other by activating an tabs of the locking mechanism. The entrapment of air bubbles into the assay area should be avoided.

The rotating plate of the cartridge is rotated at 100 rpm (+/−10 rpm) for 2 minutes as the particles and analyte mix and bind to agglutinate. Agglutinated particles are allowed to separate from non-agglutinated particles.

The cartridge is placed into a diffractometer to determine the level of agglutination present. The diffractometer takes a scan of the assay medium in an autoexpose mode with a 5× gain.

EXAMPLE 2

PARTICLE AGGLUTINATION ASSAY USING FLUID VELOCITY GRADIENTS IN A CARTRIDGE TO TEST FOR *E. COLI* WITH DRIED LATEX PARTICLES

The experiment was performed twice according to the protocol in EXAMPLE 1, with the following changes. Particles were further prepared by mixing 100 µl of each type of particle with 100 µl of 10% trehalose (D-trehalose dihydrate, provided by Aldrich Chemicals, Milwaukee, Wis. 53233, Catalog No. 18,835-2 in 10% (w/v in $dH_2O$)). Prior to adding sample to the plate, 10 µl and 6 µl aliquots of particles are spread over the raised platform of one of two separate plates. The two single plates are rotated at 100 rpm +/− rpm for one hour so that the particles are dry. Then sample is added to each one of the plates and the remaining steps are preformed according to EXAMPLE 1.Assay results are shown in FIG'S 8(*a*), 8(*b*), 8(*c*) and 8(*d*). The pictures show a clear formation of agglutinates in the positive control and a separation of those agglutinates from non-agglutinates in FIG. 8(*d*).

It is evident from the above discussion that improved agglutination assay methods and a cartridge for use is provided. The assay provides for a single-step method for mixing, rehydrating, binding particles, and separation of bound particles. Despite the simplicity of use, the assay and device provide for reliable and reproducible results.

All publications and patent applications cited in this specifications are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit and scope of the appended claims.

We claim:

1. A method for determining the presence of an analyte in a sample, where at least one selected from the group consisting of said analyte and a member of a reagent composition is a particle, and said analyte and said reagent composition member are a specific binding pair, which upon binding result in agglutination, said method comprising:

combining in an assay medium said sample and said reagent composition;

applying a circumferential fluid velocity gradient and a vertical fluid velocity gradient to said assay medium to promote mixing and binding of said analyte and said specific binding pair to form agglutinates, wherein said agglutinates form in relation to the amount of analyte present in said sample; and detecting the presence of agglutinates as indicative of the presence of analyte in said sample.

2. A method according to claim 1, wherein said assay medium has two opposing boundaries and wherein said circumferential and vertical fluid velocity gradients are created by a shear force applied to said two opposing boundaries.

3. A method according to claim 1, wherein said circumferential and vertical fluid velocity gradients are of magnitudes that allow said agglutinates to separate from said non-agglutinates.

4. A method according to claim 1, wherein said detecting of agglutinates further includes determining the sizes of said agglutinates as indicative of the present of analyte.

5. A method according to claim 1, wherein said particles are red blood cells.

6. A method according to claim 1, wherein said particles are latex particles or colloidal gold particles.

7. A method according to claim 1, wherein said reagent composition includes a cross-linking specific binding pair member.

8. A method according to claim 2, wherein at each of said opposing boundaries there is a plate and said gradients are applied by rotating at least one of said plates in a direction counter to the position of the other said plate.

9. A method according to claim 8, wherein only one of said plates is rotated.

10. A method according to claim 8, wherein both of said plates are rotated counterclockwise to each other.

* * * * *